United States Patent [19]

Handlos

[11] Patent Number: 5,251,642

[45] Date of Patent: Oct. 12, 1993

[54] TISSUE MEASURING AND SUTURING DEVICE

[75] Inventor: Kurt E. Handlos, Crestline, Calif.

[73] Assignee: Baxter International Inc., Deerfield, Ill.

[21] Appl. No.: 711,240

[22] Filed: Jun. 6, 1991

[51] Int. Cl.⁵ ............................................ A61B 5/103
[52] U.S. Cl. ...................................... 128/774; 33/512; 33/465; 33/555.2; 606/148; 606/102
[58] Field of Search ................. 128/774; 600/36; 606/57, 86, 102, 120, 152, 157, 174, 175, 205, 206, 207, 208, 209, 148; 623/13; 33/511, 512, 514.1, 555.1, 555.3, 555.2, 1 BB, 483, 458, 465; 81/342, 318-323

[56] References Cited

U.S. PATENT DOCUMENTS

| | | | |
|---|---|---|---|
| 85,553 | 1/1869 | Adams | 33/555.2 |
| 529,488 | 11/1894 | Gile | 7/131 |
| 650,793 | 5/1900 | Jones | 33/465 |
| 673,459 | 5/1901 | Stoolfire et al. | 140/121 |
| 761,272 | 5/1904 | Wagniere et al. | 33/465 |
| 924,426 | 6/1909 | Callahan et al. | 81/322 |
| 936,746 | 10/1909 | Szymanski | 33/465 |
| 2,291,413 | 2/1942 | Siebrandt | 606/86 |
| 3,176,689 | 4/1965 | Yahr | 81/318 |
| 3,258,012 | 6/1966 | Nakayama et al. | 606/150 |
| 3,588,439 | 6/1971 | Heller | 219/121.68 |
| 4,179,954 | 12/1979 | Whalen | 81/3.44 |
| 4,423,729 | 1/1984 | Gray | 606/148 |
| 4,444,180 | 4/1984 | Schneider et al. | 606/96 |
| 4,574,805 | 3/1986 | Lerner | 606/148 |
| 4,655,223 | 4/1987 | Kim | 606/148 |
| 4,686,973 | 8/1987 | Frisch | 606/95 |
| 5,018,531 | 5/1991 | Hartman | 128/774 |
| 5,070,623 | 12/1991 | Barnes | 33/807 |

*Primary Examiner*—Stephen C. Pellegrino
*Assistant Examiner*—Guy V. Tucker
*Attorney, Agent, or Firm*—Kay H. Pierce; Paul C. Flattery

[57] ABSTRACT

A scissor-like device is described which can be used to measure the diameter of a tendon graft or bone plug. The device can also be used to hold a tendon graft or bone plug in a fixed position while multiple sutures are inserted in the end thereof. The device includes a pair of arms which are hinged at the proximal end. The inner surface of each arm includes a series of semicircular sizing sleeves which mate with one another to form a series of cylindrical sleeves of increasing diameter. A tendon graft or bone plug can be placed in the series of sleeves to determine the proper diameter of the graft or plug. Various measuring indicia are provided along the arms of the device to provide an indication of both the diameter and length of tendon tissue to be measured.

23 Claims, 4 Drawing Sheets

5,251,642

TISSUE MEASURING AND SUTURING DEVICE

FIELD OF THE INVENTION

The invention generally relates to devices for sizing and measuring body tissue, and more specifically relates to devices for sizing the diameter and measuring the length of such tissue as well as for suturing the ends of such tissue at fixed predetermined locations.

BACKGROUND OF THE INVENTION

In certain orthopaedic reconstruction procedures such as a semitendinosus gracilis composite graft or a mid-third patellar tendon graft, it is necessary to remove a piece of tendon from a patient's knee area. After the tendon has been removed, it is used to replace either the anterior or posterior cruciate ligament. These tendons and ligaments are illustrated in FIG. 1. The semitendinosus gracilis composite graft is illustrated as element 12, and the mid-third patellar tendon graft is illustrated as element 14. The anterior and posterior ligaments are illustrated as elements 16 and 18.

The anterior and posterior ligaments 16, 18 are generally cylindrical ligaments. Therefore, when tendon grafts are taken to reconstruct these cruciate ligaments, it is desirable for the grafts to be uniformly cylindrical. It is also important to be able to determine the precise diameter of the tendon graft as well as the length of the graft. It is necessary to know these dimensions in order to drill a tunnel 20 (FIG. 2) through a patient's tibia and fibula which approximates the diameter of the tendon graft.

It is important that the diameter of the tunnel 20 is well matched with the diameter of the tendon graft so that the tendon is securely imbedded when inserted in the tunnel. If the tunnel is too large, irritation of the tendon may occur. This irritation may particularly occur in the area where the tibia and fibula meet and rub against each other as a patient flexes his knee. It is also important to know the precise length of the tendon in order to determine the appropriate length of the tunnel to be created. It is necessary that this tunnel be positioned to produce the optimal isometric configuration to accommodate the harvested graft.

In the past, relatively awkward devices were used to measure the diameter of a tendon graft. These devices consisted of a series of cylindrical tubes that ranged in diameter from six to fourteen millimeters in one millimeter increments. Each of these tubes were approximately two inches in length. After a tendon graft had been harvested, the graft was forced into a tube to determine if the graft had the same diameter of the tube.

Many grafts did not have uniform diameters throughout the length of the graft. Therefore, it was possible to obtain a misreading of the diameter of the graft since a portion of the graft may appear to fit snugly within the tube and comply with the sizing tube. The tubes were awkward to work with because the tendon grafts are pliable and can be difficult to insert in a tube without deforming the graft. Therefore, a need existed to develop a single device which was relatively easy to handle and could easily measure the diameter of a tendon.

As discussed above, it is also important to be able to determine the precise length of a tendon graft. In the past, a separate device, such as a simple ruler, was used to measure the length of the graft. This required that medical personnel have both a series of measuring tubes and a separate measuring tape or ruler available in the operating room to size the diameter and measure the length of a graft.

After the size of the diameter and length of a graft has been determined, a plurality of sutures are generally inserted in each end of the graft. The sutures are used to pull the graft through the tunnel and position anchor screws 22 at each end of the graft after the graft has been located in the tunnel. Generally, three sutures are placed in each end of the graft to accomplish these tasks. It is desirable that these sutures be evenly distributed at each end of the graft. This is particularly important in a bone-to-bone, mid-third patellar procedure. In the past, it has been difficult to hold the end of a bone plug while the sutures were inserted in the graft without either accidentally dropping the graft or pricking the finger of the medical personnel holding the graft. Therefore, a need existed to develop a device which held the end of a graft in a fixed position while a series of sutures were being placed in the graft without deforming or dropping the graft.

The subject invention is a single device which meets all of the needs described above. In addition, the subject invention allows medical personnel to fixate, measure, size, and suture a tendon graft or bone plug without contaminating the graft or plug or exposing it to other damage.

Thus, it was a primary object of the subject invention to provide a device for easily determining the diameter of a tendon graft or bone plug.

It was also an object of the invention to provide a device for measuring the length of a tendon graft or bone plug.

It was still another object of the invention to provide a device which may maintain the end of a tendon graft or bone plug in a fixed position while a plurality of sutures are inserted therethrough.

It was yet another object of the invention to provide a single device which accomplishes each of the tasks described above and which is easy to manipulate by medical personnel.

Other objects and many of the attendant advantages of the subject invention will become apparent from the detailed description that follows with the accompanying drawings.

SUMMARY OF THE INVENTION

A device for measuring the diameter of an object is provided. The device includes first and second arms. Each arm has a series of semicircular sizing sleeves in which each sleeve is positioned to mate with another identically sized sleeve on the other arm. The semicircular sizing sleeves mate to form circular sleeves when the arms are brought together in a closed position, in which the arms are in parallel juxtaposition with one another. In the preferred embodiment, a series of semicircular sizing sleeves are provided on each arm and the sleeves have diameters which range from six to fourteen millimeters in one millimeter increments.

In the preferred embodiment, the arms are hinged together at the proximal end of each arm with a hinge means. A gripping means is provided at the distal end of each arm to allow medical personnel to open and close the arms without touching the portion of the arms that contain the semicircular sizing sleeves.

A locking mechanism is also provided in the preferred embodiment at the distal end of each arm that interlocks when the arms are in the closed position. The locking mechanism allows the device to be maintained in the closed position without the use of additional force.

Measurement indicia indicating the diameter of each sizing sleeve is located on the device. This indicia allows medical personnel to easily determine the diameter of a tendon graft or bone plug. Also provided in the preferred embodiment is an unique length measurement indicia. The length measurement indicia extends from the distal end of one arm to at least a portion of the proximal end of the other arm and allows medical personnel to measure the length of a graft that is longer than the length of a single arm. In the preferred embodiment, the arms open outward in a "butterfly" fashion to form a straight line along the outer surface of each arm; the unique length measurement indicia is located along the outer surface of each arm.

Also included in the preferred embodiment of the subject invention is at least one cavity which extends through each of the arms at one or more of the semicircular sizing sleeves. This cavity has an axis which is perpendicular to the axis of the sizing sleeve to allow a puncturing device or suture to be inserted through the cavity and through a tendon graft or bone plug located in a sizing sleeve.

BRIEF DESCRIPTION OF THE DRAWINGS

There follows a detailed description together with accompanying drawings of a preferred embodiment of the invention. However, it is to be understood that the invention is capable of numerous modifications and variations apparent to those skilled in the art that are within the spirit and scope of the invention.

DETAILED DESCRIPTION OF THE PREFERRED EMBODIMENT

Figure 1:
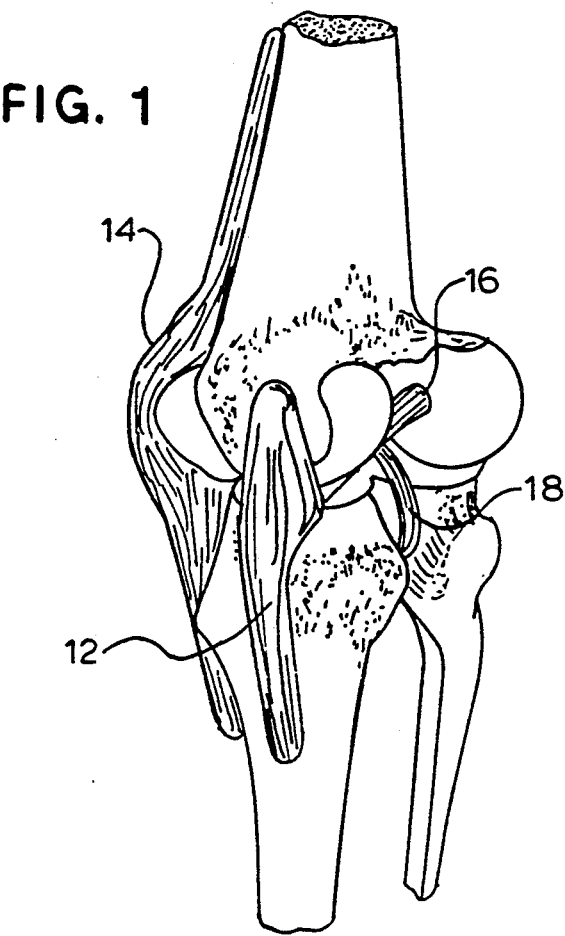
FIG. 1 is a perspective view of a patient's knee area illustrating the anterior and posterior ligaments as well as the mid-third patellar mid-section and the semitendinosus gracilis.
Figure 2:
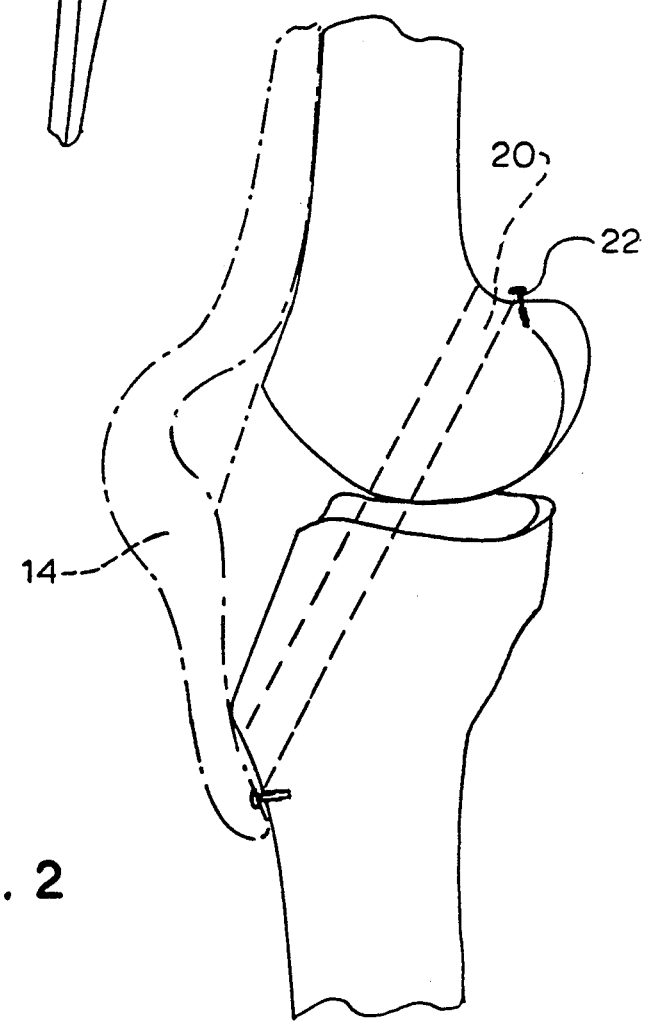
FIG. 2 is a perspective view of a patient's knee area illustrating a reconstructed tunnel configuration.
Figure 3:
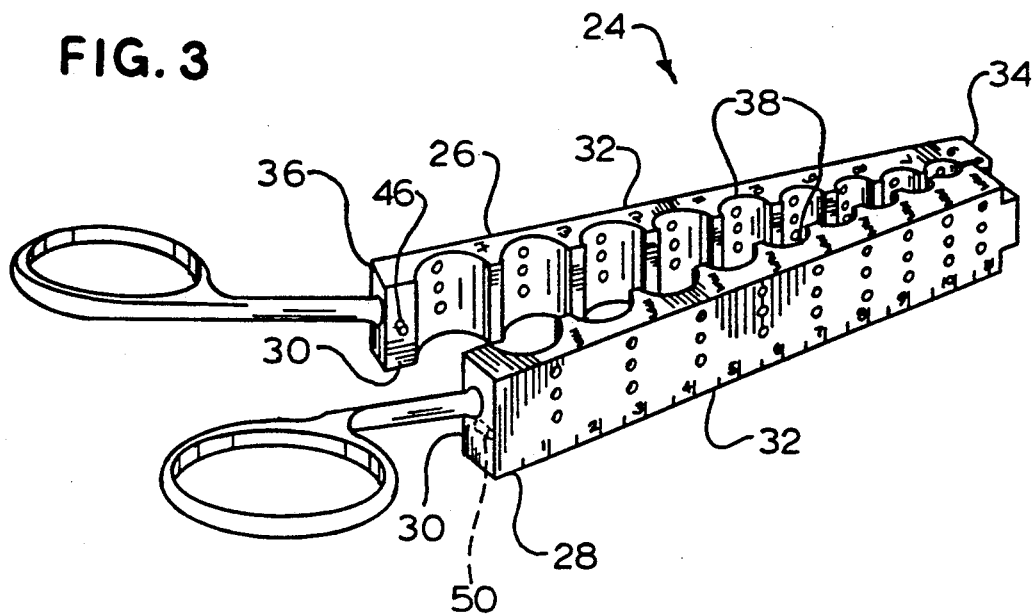
FIG. 3 is a perspective view of the preferred tendon sizing and measuring device.

Refer now to FIG. 3 which is a perspective view of the preferred embodiment of the subject device 24. As can be seen in the figure, the device 24 includes first and second arms 26, 28. Each arm has an inner surface 30, an outer surface 32, a proximal end 34, and a distal end 36. The inner surface 30 of each arm 26, 28 is provided with a series of semicircular sizing sleeves 38. Each sleeve is positioned to mate with another identically sized sleeve on the inner surface 30 of the other arm to produce a circular sizing sleeve when the first and second arms 26, 28 are placed in closed parallel juxtaposition with one another.

Figure 4:
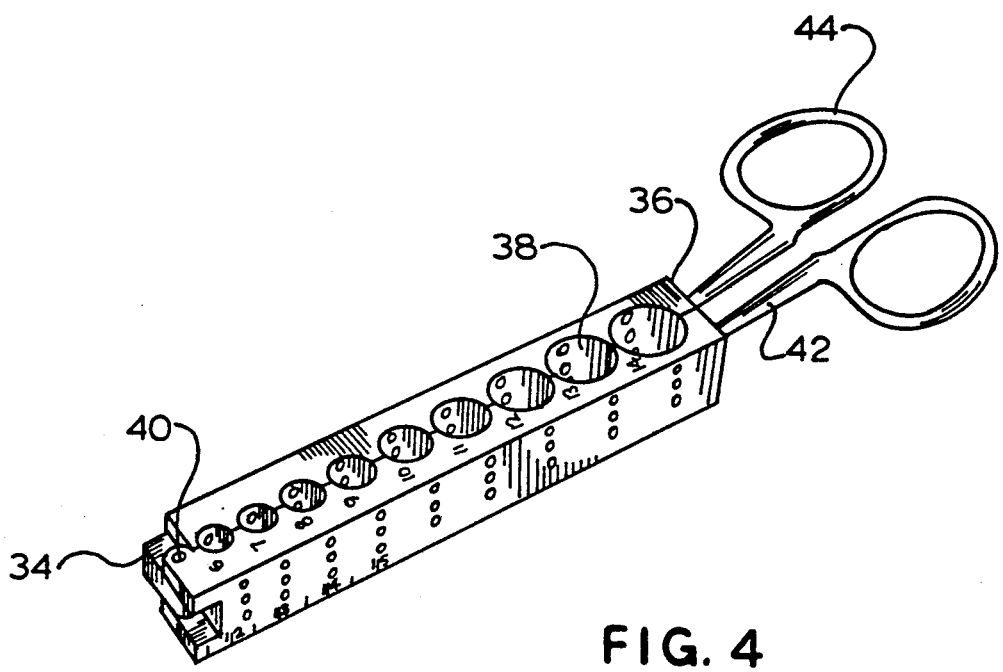
FIG. 4 is a perspective view of the arm portions of the preferred embodiment of the invention when the arms are in a closed position.

The circular sizing sleeves are illustrated in FIG. 4 which is a perspective view of a portion of the preferred embodiment of the subject invention. As can be seen in FIG. 4, a series of semicircular sizing sleeves are provided in which the diameter of each sleeve is incrementally larger than the diameter of an adjacent sleeve. In the preferred embodiment of the invention, the sleeves range in diameter from six to fourteen millimeters in increments of one millimeter.

In the preferred embodiment of the invention, the semicircular sizing sleeve having the smallest diameter is located at the proximal end 34 of each arm, and the sleeve having the largest diameter is located at the distal end 36 of each arm. This allows medical personnel to manipulate the arms without having to open the arms to an excessive amount to insert a relatively large tendon graft or bone plug in the largest sizing sleeves.

A hinge means 40 is provided at the proximal end 34 of each arm to join the proximal ends together. The arms can be opened and closed in a "scissor-like" fashion to allow medical personnel to insert a section of tendon graft or bone plug in any of the semicircular sleeves. The arms then can be closed together to determine if the tissue is the same size as the sleeve 38 by gently pulling the tissue through the sleeve 38. If the tissue is the same approximate size as the sleeve 38, a slight resistance will occur as the tissue is pulled through the sleeve. This allows medical personnel to easily determine the proper size of a drill to be used in creating a tunnel through a patient's fibula and tibia.

One of the features of the subject invention is the ability to shape a bone plug using the semicircular sleeves 38 to compress the plug into a more uniform diameter. The device can be also used to remove or scrape small portions of meaty substance from a tendon graft or bone plug by pulling the graft or plug through an appropriately sized sleeve.

In the preferred embodiment of the invention, a gripping means 42 is also provided at the distal end 36 of each of the arms. The gripping means allows medical personnel to open and close the arms without touching the portion of the arms that contain the semicircular sizing sleeves 38. In the preferred embodiment, the gripping means includes a loop handle 44 at the distal end 36 of each of the arms. Medical personnel can insert a finger or thumb through each loop handle 44 to open and close the arms with a single hand. This allows a medical personnel to easily grip the tendon graft or bone plug in one hand while manipulating the subject device with the other hand to determine the size of the diameter of a graft or plug.

In one embodiment of the invention, a locking means 46 is provided to stabilize the arms in a closed position. The locking means 46 allows medical personnel to close the arms of the device and maintain the arms in a closed position without the use of additional force. In the preferred embodiment of the invention, the locking means 46 includes a spring-loaded pin 48 at the distal end 36 of one of the arms 28 and a mating orifice 50 at the distal end of the other of the arms 26. The pin 48 and the orifice 50 interlock with each other when the arms are in a closed position.

Figure 7:
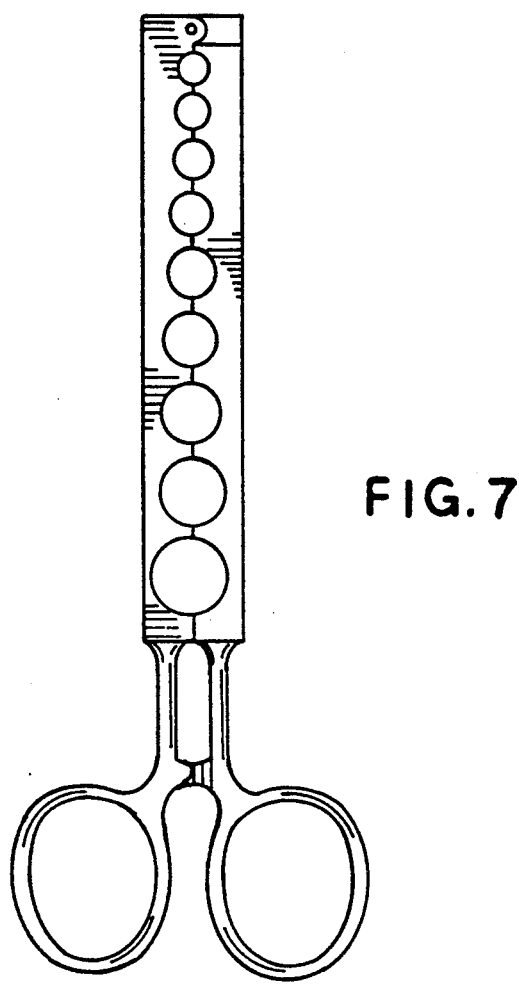
FIG. 7 illustrates another embodiment of the invention in which a ratchet means is used to maintain the arms of a device in a closed position.

In another embodiment of the invention, a ratchet means such as those commonly used with hemostats may be provided to lock the device in a closed position. Such a ratchet means is illustrated in FIG. 7.

Figure 5:
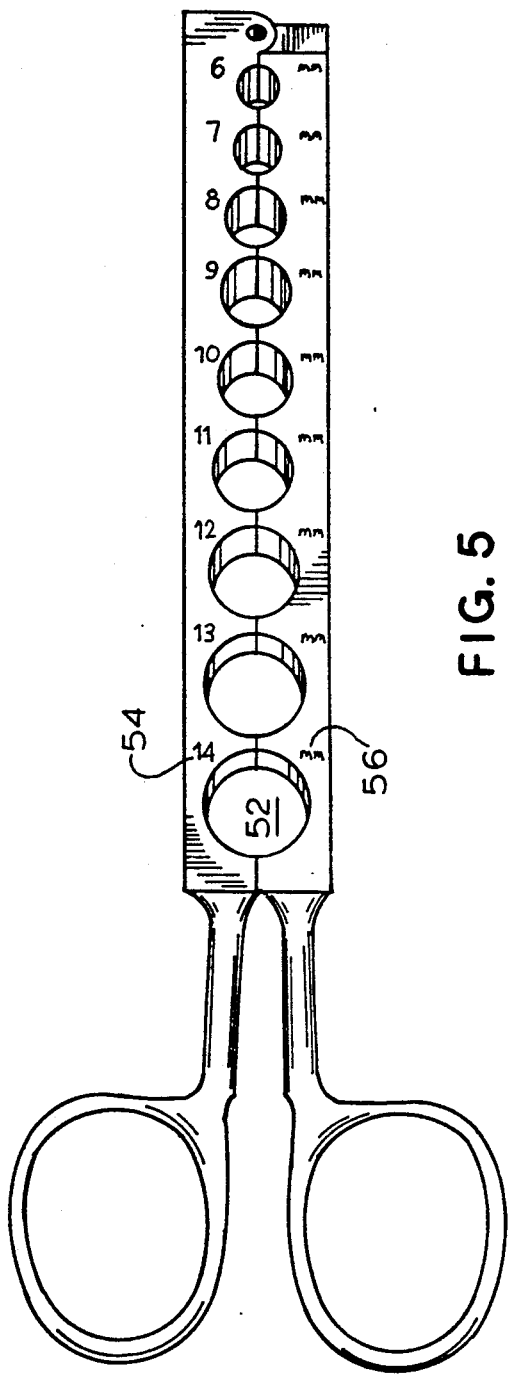
FIG. 5 is another perspective view of the arm portions of the device illustrating diameter measuring indicia.

Refer now to FIG. 5 which is another perspective view of the preferred embodiment of the subject invention. As can be seen in the figure, diameter measurement indicia 52 is provided to indicate the diameter of each semicircular sizing sleeve. In the preferred embodiment of the invention, the measurement indicia 52 includes a numerical indication 54 of the diameter of each sleeve on one of the arms and an indication of the unit of numerical measurement 56 on the other of the arms.

Also, in the preferred embodiment, the measurement indicia is laser engraved on each of the arms. The advantage of laser engraving the indicia is that it creates a smooth engraved etching which can be readily sterilized by a variety of means. The laser engraving is also beneficial in that it provides a smooth surface texture which can be easily read by medical personnel and is not subject to fading or general wear.

Figure 6:
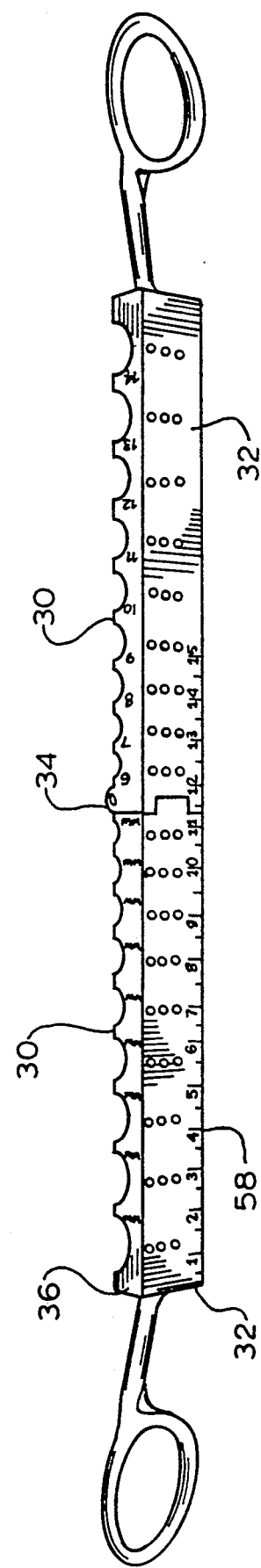
FIG. 6 is a perspective view of the subject device in which the arms are in a fully opened, butterfly position.

The subject invention also includes a unique method of measuring the length of a tendon graft or bone plug. This can be seen in FIG. 6, which is a perspective view of the subject invention in which the arms are in a completely open or "butterfly" position. As can be seen in the figure, the arms of the subject device can be moved from a closed position in which the inner surfaces 30 are closed upon one another to an open, butterfly position in which the outer surfaces 32 extend to form a straight line. The outer surfaces 32 are provided with linear measurement indicia 58 that extend continuously from a distal end 36 of one arm to at least a portion of a proximal end 34 of the other arm. Thus, the linear measurement indicia 58 can be substantially longer than the length of a single arm. By opening the arms to a completely open butterfly position, it is possible to provide a measuring device which can measure tendon grafts or bone plugs that are up to twice as long as the length of a single arm.

The subject invention is unique in that it uses the outer surfaces of each arm to provide a means of measuring the length of a bone plug or tendon graft while it uses the inner surface of each arm to measure the diameter of the same plug or graft. Thus, a single device can be used to perform functions that were previously performed by multiple devices. This greatly simplifies the sizing and measuring of a bone plug or tendon graft during a medical procedure. This device also improves the accuracy of measurement and enhances the ability of medical personnel to handle a graft or plug without damaging or dropping the tissue.

As can be seen in FIG. 7, one of the features of the subject invention is that the sizing sleeves can be used to hold body tissue in a fixed position. This is accomplished by inserting the tissue in a sizing sleeve which is slightly smaller than the diameter of the tissue to be held. When the arms are in a closed position, the tissue is snugly held in the sizing sleeve through compressive forces.

This ability to hold tissue snugly in a sizing sleeve is very important. It allows medical personnel to insert sutures into one end of the tissue without exposing the medical personnel's hands to the possibility of needle sticks. This is important in view of the desire to prevent transmitting AIDS or other communicable diseases through accidental needle sticks. The ability to snugly hold tissue while inserting sutures is also important in preventing accidental droppage of the tissue which would prevent it from being used for reconstructive purposes and would considerably complicate the outcome of the procedure.

In the preferred embodiment of the invention, means are provided for enhancing the ability of medical personnel to insert sutures in the ends of relatively impermeable body tissue, such as tendon grafts and bone plugs. Specifically, at least one cavity 60 is provided which extends through each of the arms at a semicircular sizing sleeve. The cavity has an axis which is perpendicular to the axis of the sizing sleeve. Medical personnel can insert a puncturing device through the cavity and through any tissue located in the sizing sleeve. This cavity provides a means for accurately locating the position of a suture in the end of a tendon graft or bone plug.

In the preferred embodiment of the invention, a series of three cavities 62 extend through each of the arms in vertical alignment at each semicircular sizing sleeve. The cavities are spaced apart from each other at a predetermined distance to provide a highly accurate method of locating a series of sutures at each end of a bone plug or tendon graft. In the preferred embodiment, the cavities are located 3/16ths of an inch apart from one another.

As discussed above in the Background of the Invention, the sutures are used to pull a tendon graft or bone plug through a tunnel and position each end of the graft or plug. The sutures are used to pull on the opposite ends of the graft or plug once it has been inserted in the tunnel to create a desired amount of tension on the graft or plug prior to permanent anchoring of the graft or plug. The sutures can then be wrapped around anchoring screws to provide additional security in maintaining the implanted tissue in the proper location.

Figure 8:
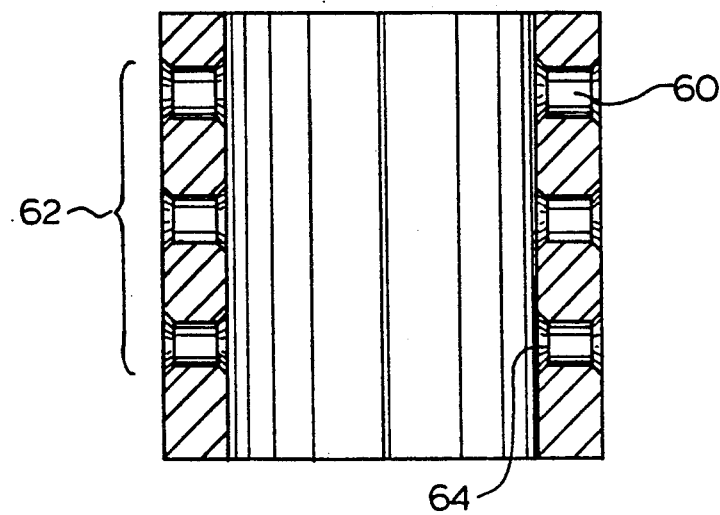
FIG. 8 illustrates a chamfered edge of a suture cavity.

In the preferred embodiment of the invention, the cavity is chamfered at the interface between the inner surface of each arm and the cavity 64 to provide a guide for centering a puncturing device. This forces a puncturing device toward the center of each cavity when it is inserted through the cavity. This is illustrated in FIG. 8.

A variety of materials can be used to manufacture the subject device. In general, it is desired that the material be of a high corrosion resistant composition. In the preferred embodiment of the invention, a 316 U.S. standard steel grade was chosen.

While the invention has been described in detail and with reference to specific embodiments thereof, it will be apparent to those skilled in the art that various changes and modifications can be made therein without departing from the spirit and scope of the invention.

I claim:

1. A medical device for measuring the diameter of a piece of body tissue, comprising:
   first and second arms, each arm having a series of semicircular shaped sizing sleeves, each sleeve on one arm being positioned to mate with another identically sized sleeve on the other arm to provide a circular sizing sleeve when said first and second arms are placed in parallel juxtaposition with one another, and
   a means for allowing puncture of said tissue, said means for allowing puncture located through at least one of said arms at at least one of said semicircular shaped sizing sleeves.

2. A medical device as recited in claim 1, wherein said series of semicircular shaped sizing sleeves have diameters which range from a maximum value to a minimum value in predetermined increments.

3. A medical device as recited in claim 2, wherein said predetermined increments of said series of semicircular shaped sizing sleeve increase in value by one millimeter increments and range from six to fourteen millimeters.

4. A medical device as recited in claim 2, wherein said semicircular shaped sizing sleeve having a minimum value is at a proximal end of each of said arms, and said device further comprises:
a hinge means for joining said proximal ends of each arm to one another.

5. A medical device as recited in claim 4, further comprising:
gripping means for providing a gripping location to allow opening and closing of said arms without touching the portion of said arms having said semicircular shaped sizing sleeves.

6. A medical device as recited in claim 5, wherein:
said gripping means includes a loop handle at the distal end of each of said arms to allow a user to insert a finger through each loop to open and close said arms.

7. A medical device as recited in claim 4, further comprising:
locking means for stabilizing said arms in a closed position.

8. A medical device as recited in claim 7, wherein:
said locking means includes a spring loaded pin at the distal end of one of said arms and mating orifice in the distal end of the other of said arms to interlock when said arms are in a closed position.

9. A medical device as recited in claim 1, further comprising:
measurement indicia indicating the diameter of each semicircular shaped sizing sleeve.

10. A medical device as recited in claim 9, wherein said measurement indicia includes:
a numerical indication of the diameter of each sleeve on one of said arms, and
an indication of the unit of numerical measurement on the other of said arms.

11. A medical device as recited in claim 9, wherein said measurement indicia is laser engraved on said arms.

12. The medical device of claim 1, wherein the body tissue is a tendon.

13. The medical device of claim 1, wherein the body tissue is bone.

14. A medical device for holding body tissue, comprising:
first and second arms, each arm having a distal and proximal end;
hinge means at said proximal end of each arm to allow said arms to open and close on one another;
a series of pairs of mating semicircular shaped sizing sleeves so constructed and arranged for holding tissue therein, one of said mating semicircular sleeves of a pair being located on said first arm and the other of said mating semicircular sleeves of a pair being located on said second arm such that when said arms are closed, said sleeves are in registry to define a tubular opening, said sleeves being slightly smaller than the diameter of the tissue to be held so that when the tissue is inserted between said arms at said sizing sleeves and said arms are closed, said tissue is held between said arms in said sleeves by compression; and
a means for allowing puncture of said tissue, said means for allowing puncture located through at least one of said arms at at least one of said semicircular shaped sizing sleeves.

15. A medical device for holding body tissue, as recited in claim 14, wherein said means for allowing puncture further comprises:
at least one cavity extending through each of said arms at at least one of said semicircular shaped sizing sleeves, said cavity having an axis perpendicular to said axis of said sizing sleeves and constructed to allow said tissue to be punctured through said cavity when said tissue is held in said arms at said sizing sleeve.

16. A medical device as recited in claim 14, further comprising:
a series of cavities extending through each of said arms at said semicircular shaped sizing sleeves, said cavities each having an axis perpendicular to said axis of said sizing sleeves and so constructed and arranged to allow puncture of said cavities and said tissue at a predetermined location when said tissue is held in said arms at said sizing sleeves.

17. A medical device as recited in claim 16, wherein each arm has an inner surface and an outer surface and each of said cavities is chamfered at said inner surface of each arm to facilitate puncturing of said tissue toward the center of each cavity when puncturing tissue is held in said arms.

18. A device for holding body tissue, comprising:
first and second arms, each arm having a distal and proximal end;
hinge means at said proximal end of each arm to allow said arms to open and close on one another;
at least one pair of semicircular shaped sizing sleeves constructed for holding tissue therein, one of said sleeves being located on said first arm and the other of said sleeves being located on said second arm such that when said arms are closed, said sleeves are in registry to define a tubular opening within which tissue can be held, said sleeves being slightly smaller than the diameter of the tissue to be held so that when the tissue is inserted between said arms at said sizing sleeves and said arms are closed, said tissue is held between said arms in said sleeves by compression; and
a series of three cavities extending through each of said arms at said semicircular shaped sizing sleeves, each of said cavities having an axis perpendicular to an axis of said sizing sleeve and so constructed and arranged to allow said tissue to be punctured through each of said cavities at a predetermined location when said tissue is held in said arms at said sizing sleeve, said cavities being located to allow sutures to be inserted in a tissue at a fixed predetermined distance from one another.

19. A device for compressing a bone plug to enhance uniformity of said plug, comprising:
first and second arms hingedly attached at longitudinal ends thereof to allow said arms to be closed upon each other;
said arms having a series of mating semicircular shaped sleeves that form circular sleeves of different diameters when the arms are closed and that are slightly smaller than said bone plug to compress said plug when said plug is inserted between said arms at said sleeves and said arms are closed upon each other to compress said plug into a uniform circumference; and
means located through at least one of said arms on said sleeves for allowing puncture of said bone plug when said bone plug is inserted between said arms.

20. A medical device for measuring the length of a piece of body tissue, comprising:

first and second arms, said arms having an inner surface and an outer surface, said arms being hinged together at proximal ends thereof to allow said arms to be moved from a closed position in which said inner surfaces are closed upon one another to an open, butterfly position in which said outer surface of both arm extends in a straight line to allow said outer surfaces to form a ruler, wherein each arm includes a series of semicircular shaped sizing sleeves, each sleeve being positioned to mate with another identically sized sleeve on the other arm to provide a circular sizing sleeve when said first and second arms are placed in parallel juxtaposition with one another;

measurement indicia engraved upon said outer surfaces and extending continuously from a distal end of one arm to at least a portion of said proximal end of said other arm to allow a length of body tissue that is longer than the length of one arm to be accurately measured; and a series of cavities extending through each of said arms at said semicircular shaped sizing sleeve, said cavities each having axis perpendicular to said axis of said sizing sleeve to allow puncture of said cavities and said tissue at a predetermined location when said tissue is held in said arms at said sizing sleeve.

21. A medical device as recited in claim 20, further comprising:

gripping means for providing a gripping hold to open and close said arms without touching the portion of said arms having said semicircular shaped sizing sleeves.

22. A device as recited in claim 20, further comprising:

locking means for stabilizing said arms in a closed position, said locking means includes a spring loaded pin at the distal end of one of said arms and mating orifice in the distal end of the other of said arms to interlock when said arms are in a closed position.

23. A medical device, comprising:

first and second arms, each arm having distal and proximal ends;

hinge means joining proximal ends of said arms to allow said arms to open and close on one another;

at least one pair of semicircular shaped sizing sleeves located on said arms, one of said sleeves being located on said first arm and the other of said sleeves being located on said second arm such that when said arms are closed, said sleeves are in registry to define a tubular opening, said sleeves being constructed for holding tissue therein, said sleeves being slightly smaller than the diameter of the tissue to be held so that when the tissue is inserted between said arms at said sizing sleeves and said arms are closed, said tissue is held between said arms in said sleeves by compression;

a series of cavities extending through each of said arms at said semicircular shaped sizing sleeves, said cavities each having an axis perpendicular to an axis of said sizing sleeves and constructed to allow puncture of said cavities and said tissue at a predetermined location when said tissue is held in said arms of said sizing sleeves;

a measurement indicia engraved upon an outer surface of said first and second arms and extending continuously from a distal end on one arm to at least a portion of said other arm to allow a length of body tissue that is longer than the length of one arm to be accurately measured;

gripping means attached to said first and second arms for providing a gripping hold to open and close said arms without touching the portion of said arms having said semicircular shaped sizing sleeves; and locking means for stabilizing said arms in a lock position.

* * * * *